United States Patent [19]

Bogdanović

[11] Patent Number: 4,731,203
[45] Date of Patent: Mar. 15, 1988

[54] PROCESS FOR USING FINELY DIVIDED HIGHLY REACTIVE MAGNESIUM

[75] Inventor: Borislav Bogdanović, Mülheim/Ruhr, Fed. Rep. of Germany

[73] Assignee: Studiengesellschaft Kohle mbH, Mulheim/Ruhr, Fed. Rep. of Germany

[21] Appl. No.: 895,658

[22] Filed: Aug. 12, 1986

Related U.S. Application Data

[62] Division of Ser. No. 669,209, Nov. 7, 1984, Pat. No. 4,659,373.

[30] Foreign Application Priority Data

Nov. 9, 1983 [DE] Fed. Rep. of Germany ....... 3340492

[51] Int. Cl.$^4$ ............................................. C07F 3/02
[52] U.S. Cl. .................. 260/665 G; 568/12; 568/851
[58] Field of Search .............. 260/665 G; 568/12, 851

[56] References Cited

U.S. PATENT DOCUMENTS

| | | | |
|---|---|---|---|
| 2,056,822 | 10/1936 | Britton et al. | 260/665 G |
| 2,921,940 | 1/1960 | Ramsden | 260/665 G X |
| 2,943,115 | 6/1960 | Normant | 260/665 G |
| 3,193,375 | 7/1965 | Marx et al. | 75/0.5 B |
| 3,247,297 | 4/1966 | Salesse et al. | 75/0.5 B |
| 3,714,246 | 1/1973 | Smith et al. | 568/12 X |
| 3,969,104 | 7/1967 | Barannik et al. | 75/0.5 B |
| 4,541,867 | 9/1985 | Neelameggham et al. | 75/0.5 A |
| 4,543,122 | 9/1985 | Bodenstein et al. | 75/0.5 B |

OTHER PUBLICATIONS

Chemical Abstracts, 88, 37864c, (1978).
Index Chemicus, 19(1), 5655o, (1965).
Kharasch et al., Grignand Reactions of Nonmetallic Substances, Prentice-Hall, Inc., New York, pp. 17, 18, 19, 22, 27, 28, 29, 32 and 36, (1954).

Primary Examiner—Helen M. S. Sneed
Attorney, Agent, or Firm—Sprung Horn Kramer & Woods

[57] ABSTRACT

The present invention relates to a process for preparing a finely divided, highly reactive magnesium from magnesium hydride, magnesium anthracene and/or its derivatives or magnesium butadiene and/or its alkyl or phenyl derivatives, which process is characterized in that the respective magnesium-containing compound is thermally decomposed at a pressure from $10^{-6}$ to 1 bar, the decomposition being carried out in the presence of a co-reactant of a consecutive reaction, or such co-reactant being added only after completion of the precipitation of the magnesium, or in the absence of such co-reactant, the magnesium obtained by said decomposition being isolated as a powder, and to the use of the finely divided, highly reactive magnesium for inserting magnesium into poorly reactive C—X bonds, wherein X denotes heteroatoms such as halogen, oxygen, sulfur, nitrogen, phosphorus, and the resulting organomagnesium compound may be used in a consecutive reaction according to a per se known method, and for the reversible preparation of active magnesium hydride by reaction with molecular hydrogen at a pressure of from 1 to 2 bar and at a temperature of from 150° C. to 250° C.

9 Claims, No Drawings

PROCESS FOR USING FINELY DIVIDED HIGHLY REACTIVE MAGNESIUM

This is a division of application Ser. No. 669,209, filed Nov. 7, 1984, now U.S. Pat. No. 4,659,373.

The invention relates to a process for preparing a finely divided, highly reactive magnesium and the use thereof.

Activated forms of metallic magnesium are used to an increasing extent in chemical syntheses, more specifically for Grignard reactions, as reducing agents, for dehalogenation reactions and the like. Thereby, most of said reactions can be effected with a substantially higher efficiency than, e.g., by using commercially available magnesium powder, while other reactions have only become realizable therewith (cf., e.g., Y.-H. Lai, Synthesis 585 (1981); W. Oppolzer in "Current Trends in Organic Synthesis", Ed. H. Nozaki, Pergamon Press 1983, p. 131). According to R. D. Rieke, magnesium can be obtained in an active form by reduction of magnesium halides with alkali metals, more particularly with potassium, in tetrahydrofuran (THF) (Acc. Chem. Res. 10, 301 (1977)) or 1,2-dimethoxyethane, optionally with the addition of naphthalene as an electron transfer agent (Arnold & Kulenović, Synth. Commun. 7, 223 (1977); Rieke et al., J. Org. Chem. 46 4323 (1981). These methods have disadvantages inasmuch as that activated magnesium is obtained suspended in THF or 1,2-dimethoxyethane as a mixture with the respective alkali metal halide and mostly also with the alkali metal so that for the preparation of active magnesium by said route equimolar amounts of alkali metal, e.g. metallic potassium, are required.

It is the object of the present invention to provide a process for the preparation of highly active magnesium, which process is free from the aforementioned drawbacks and, in addition, is suitable for being carried out on a larger scale.

There has been known that an equilibrium exists between metallic magnesium and hydrogen, on the one hand, and magnesium hydride, on the other hand, which equilibrium inherently is temperature-dependent and reversible:

$$Mg + H_2 \rightleftharpoons MgH_2, \Delta H = -74.8 \text{ kJ/mol} \quad (1)$$

At room temperature and under regular pressure, the equilibrium of equation (1) is almost completely on the magnesium hydride side. With increasing temperature, the hydrogen partial pressure of magnesium hydride increases and, for example, reaches the values of 1, 2 and 5.5 bar at a temperature of 284° C., 310° C. and 350° C., respectively. However, the hydrogenation of commercially available magnesium in the absence of catalysts well as the thermal decomposition of the formed magnesium hydride proceed at an extremely low speed even at a temperature of about 400° C. (cf., e.g., Stander, Z. für physikal. Chem. Neue Folge 104, 229 (1977)). In addition, in the thermal decomposition of the magnesium hydride prepared at a high temperature there is formed a magnesium metal having a low chemical reactivity, so that said route will hardly be suitable as a method for activating magnesium.

According to the European Patent Specification No. 0 003 564 (to Applicants) a process has become known which allows magnesium to be hydrogenated to give magnesium hydride under mild conditions (e.g., at from 20° C. to 60° C. and from 1 to 80 bar) by means of the homogeneous catalysts as described therein.

Now, surprisingly there has been found that a finely divided, highly reactive magnesium suspended in a solvent or, upon respective work-up, a pyrophoric magnesium powder having an unexpectedly high chemical reactivity is formed, when said magnesium hydride generated in the presence of a homogeneous catalyst is thermally dehydrogenated. Therefore, a method according to the invention for preparing a highly reactive and very finely divided magnesium comprises the thermal dehydrogenation under reduced pressure of magnesium hydride having been prepared according to a per se known process.

According to the U.S. Pat. Nos. 3,351,646, 3,354,190 and 3,388,179 metallic magnesium in THF will undergo an addition reaction to anthracene and other condensed aromatic ring systems and to butadiene and other conjugated dienes to form the corresponding magnesium adducts of said hydrocarbons, magnesium anthracene, magnesium butadiene etc. In accordance with our findings, the adducts magnesium anthracene.3 THF, magnesium butadiene.2 THF etc. are in a temperature-dependent, reversible equilibrium with their respective organic constituents and magnesium metal (Eqns. 2 and 3, respectively), a low temperature favoring the adduct formation.

There has now surprisingly been found that a finely divided, highly reactive magnesium suspended in a solvent or, upon respective work-up, a magnesium powder having an extremely high chemical reactivity is formed, when magnesium anthracene, magnesium butadiene and/or adducts of magnesium to other conjugated dienes having the general formula $R^1$—CH=C-$R^2$—CH=CH—$R^3$, wherein $R^1$, $R^2$ and $R^3$ may be same or different and represent H, a linear or branched alkyl group having from 1 to 6 carbon atoms or a phenyl residue, are decomposed to form metallic magnesium upon shifting the equilibria shown by the following equations 2 and 3 from the right to the left by raising the temperature and/or reducing the concentrations of anthracene and THF, or diene and THF, respectively.

(2)

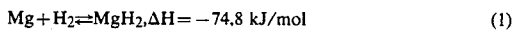

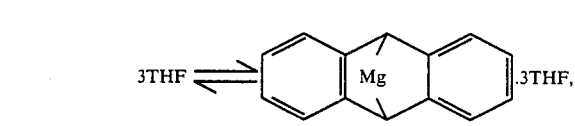

(3)

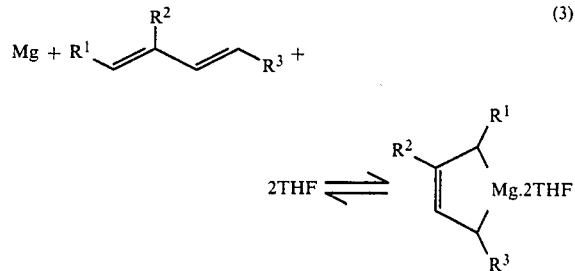

Therefore, another method according to the invention for activating magnesium comprises first reacting a commercially available magnesium in a per se known manner with anthracene, butadiene or a different conjugated dienes having the general formula $R^1$—CH=C-$R^2$—CH=CH—$R^3$, wherein $R^1$, $R^2$ and $R^3$ may be same or different and represent H, a linear or branched alkyl group having from 1 to 6 carbon atoms or a phenyl residue, in THF to form magnesium anthracene.3 THF, magnesium butadiene.2 THF etc. (shifting the equilibria according to the equations 2 and 3, respectively, from the left side to the right side) and subsequently producing the activated magnesium by increasing the temperature and/or reducing the concentrations of anthracene and THF or diene and THF etc. (shifting back the equilibria according to the equations 2 and 3, respectively, from the right side to the left side) in accordance with the instant process.

In a preferred embodiment of the present invention one procedure for activating the magnesium comprises hydrogenating commercially available magnesium according to the process described in the European Patent Specification No. 0 003 564 to form magnesium hydride and subsequently thermally dehydrogenating the magnesium hydride having been thus produced at a temperature in excess of 300° C. under atmospheric pressure, and preferably in excess of 250° C. under reduced pressure. The hydrogen obtained thereby may be conveniently recycled and used for hydrogenating another magnesium batch in accordance with the homogeneously catalytic process according to the EP-A No. 0 003 564, whereby an economic process for preparing activating magnesium from commercially available magnesium has been provided.

In a further preferred embodiment of the present invention a commercially available magnesium is reacted in a per se known step with anthracene or one of its alkyl or phenyl derivatives according to equation (2), or with a conjugated diene having the general formula $R^1$—CH=$CR^2$—CH=CH—$R^3$, wherein $R^1$, $R^2$ and $R^3$ may be same or different and represent H, a linear or branched alkyl group having from 1 to 6 carbon atoms or a phenyl residue according to equation (3), and the resulting organomagnesium compound is thermolyzed at an elevated temperature in vacuo or at atmospheric pressure.

The preferred range of temperatures for the decomposition of magnesium anthracene.3 THF or of magnesium adducts to substituted anthracenes in the solid state is between +70° C. and +170° C. In an inert organic solvent the decomposition is effected under atmospheric pressure at a temperature of from +20° C. to +100° C. As the inert organic solvents there may be used aliphatic, cycloaliphatic and aromatic hydrocarbons as well as open-chain aliphatic ethers such as diethyl ether and dibutyl ether.

The preferred reaction temperature for the decomposition of magnesium butadiene.2 THF and of magnesium adducts to optionally substituted conjugated dienes, e.g. 1,4-diphenylbutadiene or isoprene, are from +20° C. to +150° C. As a solvent there is used one of the above-mentioned inert organic solvents.

In the place of magnesium anthracene or magnesium butadiene, respectively, there may also be employed the magnesium adducts to the alkyl or phenyl derivatives thereof, e.g. 1,4-diphenyl butadiene or isoprene, for the preparation of finely divided, reactive magnesium, while in the place of THF as a solvent there may be used 2-methyltetrahydrofurane or THF in combination with N,N,N',N'-tetramethylethylenediamine (TMEDA) or 1,2-dimethoxyethane.

The decomposition of said thermolabile organomagnesium compounds may optionally be accelerated by means of a catalyst or promoter which, in addition, possibly may positively affect the properties of the active magnesium (particle size, particle shape, (specific) surface area, type and amount of adsorbed materials); organic halogen compounds, e.g. ethylbromide, 1,2-dichloroethane and 1,2-dibromoethane, and magnesium halides may be used as such compounds.

The decomposition of the thermolabile organomagnesium compounds to form highly reactive magnesium optionally may also be accelerated by some physical technique (ultrasonic treatment, light irradiation, mechanical effects).

The formation of active magnesium may be effected in the presence of the materials which are to react with the active magnesium (such as, e.g., organic halogen or phosphorus compounds) or to interact with the active magnesium (such as, e.g., inorganic carriers at the surface of which the active magnesium is to be adsorbed). In these cases the active magnesium may be produced at a temperature substantially lower than +20° C., e.g. at −70° C. or even less, as it is continuously removed from the equilibrium state (equations 2 or 3, respectively) by the direct reaction with the reactants, e.g. the organic halogen or phosphorus compounds.

On the other hand, the materials with which the highly active magnesium powder prepared according to the invention is intended to react may also be added to the system after the deposition of the active magnesium has been completed. Upon completion of one cycle of the preparation of the active magnesium, the recovered organic components anthracene, butadiene, THF etc. may be employed to activate another magnesium batch, which process may optionally be operated in a circulation system.

The active magnesium obtainable by the process according to the invention is distinguished by having a particularly high (specific) surface area; thus, e.g., the specific surface area of the magnesium as produced by the thermal decomposition of magnesium anthracene.3 THF under vacuum is 62 $m^2/g$.

The high chemical reactivity, as compared to that of commercially available magnesium powder, of the magnesium obtainable by the present process, is evident from, inter alia, that it can be inserted in poorly reactive C—X bonds wherein X denotes hetero atoms such as halogen, oxygen, sulfur, nitrogen, phosphorus and the like.

Thus, the active magnesium obtained by the thermolysis of the magnesium hydride prepared in the homogeneous catalytic reaction does already react in THF under mild conditions with aryl chlorides, which are believed to be particularly non-reactive in the Grignard reaction, to form the corresponding Grignard compounds in high yields. Allyl chlorides can be converted into the Grignard compounds by means of the active magnesium obtained by the process according to the invention at a temperature as low as −50° C., whereby the Wurtz dimerization of the organic radicals which at higher temperatures increasingly interferes with the conventional Grignard reactions can be almost completely suppressed. For the preparation of the allyl Grignard compounds, there is preferably employed the variant of the process according to the present invention wherein the highly reactive magnesium is produced at a low temperature in the presence of the respective allyl halide.

There has further been known from the literature (and confirmed by my own control experiments) that isobutyl chloride does not react nor form organomagnesium compounds with normal magnesium in hydrocarbons (D. B. Malpass et al. in Kirk-Othmer, Encycl. Chem. Techn., Vol. 16, 3rd edition, p. 555). In the reaction of isobutyl chloride with active magnesium, obtained by thermolysis of magnesium anthracene in toluene or heptane, respectively, isobutyl magnesiumchloride was obtained in a yield of about 30% (no optimization was attempted in the experiments).

The high reactivity of the active magnesium obtainable by the thermolysis of magnesium hydride prepared in the homogeneous catalytic reaction or of the magnesium anthracene or magnesium diene, respectively, is particularly clearly demonstrated by its cleavage reaction with THF with inserting the metal into a carbon-oxygen bond to form 1-oxa-2-magnesia-cyclohexane.

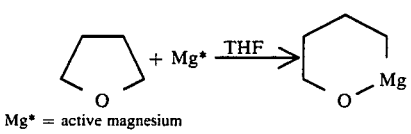

Mg* = active magnesium

Conventional types of magnesium are considered to be inert to THF; the formation of the 1-oxa-2-magnesia-cyclohexane by cleavage of THF with metallic magnesium so far has only been observed when "Rieke magnesium" (Bickelhaupt et al., Heterocycles 7, 237 (1977)) was employed.

The results of several experiments show that 1-halogenophospholenium-halides (such as, e.g., 1) can be reduced with active magnesium obtained according to the invention from magnesium hydride produced in the homogeneous catalytic reaction to give the corresponding 3-phospholenes (2) at lower reaction temperatures and with substantially higher yields than has been possible by means of the reductions using normal magnesium having so far been described (L. D. Quinn et al., Tetr. Lett. 26, 2187 (1965)).

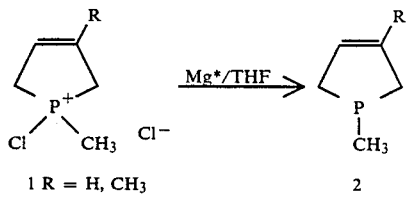

1 R = H, CH₃  2

The high reactivity of the active magnesium having become accessible by the process according to the present invention is also demonstrated by the fact that it absorbs hydrogen at a temperature in excess of 150° C. at atmospheric pressure slowly (under a pressure of 2 to 3 bar rapidly) to form magnesium hydride without any need of adding an activator such as, e.g., in the EP-A No. 0 003 564. These conditions are the mildest conditions under which magnesium has ever been hydrogenated. Commercially available magnesium requires drastic reaction conditions to be applied in order to accomplish the hydrogenation.

The present invention is further illustrated by, while not limited to, the following examples. All experiments described in the Examples have been carried out under argon as protective gas.

EXAMPLE 1

A glass vessel containing 32.0 g of magnesium hydride prepared according to the EP-A No. 0 003 564 using a chromium catalyst (Mg:anthracene:$CrCl_3$=100:1:1; 60° C./20 bar) was heated in an electrically heatable autoclave at from 0.2 to 10 mbar to reach a temperature of 350° C. within 2 hours and then maintained at said temperature until the hydrogen evolution had ceased. The organic components as contained in the reaction mixture were volatilized in excess of 100° C., while the endothermic hydrogen evolution started at a temperature in excess of 250° C. Upon cooling, 28.6 g of a gray pyrophoric magnesium powder were obtained which had the following composition: Mg 94.5, C 1.4, H 1.3, Cl 2.2, Cr 0.5%.

Grignard compounds made from active magnesium: To the suspension of 3.05 g (117 mmol) of the thus obtained magnesium powder in 50 ml THF there were dropwise added 100 mmol of the aryl chloride or allyl chloride RCl as set forth in the following Table at the temperature indicated in the Table. After another 30 minutes (during which the temperature was kept constant in the case of the aryl chlorides and was slowly raised to −10° C. in the case of the allyl chlorides) there was reacted with the respective electrophile and worked up in the conventional manner. The products were identified by comparison of their melting points or boiling points, respectively, IR spectra and ¹H-NMR spectra with data reported in the literature.

TABLE

| RCl | T (°C.) | Elektrophil | Product | Yield (%)[a] |
|---|---|---|---|---|
| $C_6H_5Cl$ | 0 | $CO_2/H_3O^+$ | $C_6H_5COOH$ | 77 |
| $C_6H_5Cl$ | 0 | $ClSi(CH_3)_3$ | $C_6H_5Si(CH_3)_3$ | 67 |
| 1-chloronaphthalene | +45 | $H_3O^+$ | naphthalene | 82 |
| $CH_2=CHCH_2Cl$ | −50 | $CO_2/H_3O^+$ | $CH_2=CHCH_2COOH$ | 83 |
| $CH_3\text{-}CCH_2Cl$ (with $CH_3$) | −50 | $CO_2/H_3O^+$ | $CH_2=CCH_2COOH$ (with $CH_3$) | 72 |

[a]based on a chloride used as the starting material.

EXAMPLE 2

Reaction of the active magnesium with tetrahydrofuran to form 1-oxa-2-magnesia-cyclohexane: A suspension of 2.43 g (95 mmol) of the active magnesium prepared as described in Example 1 in 75 ml THF was heated to reflux for some days.. During this period, samples were taken from the solution at defined intervals, hydrolyzed and the yield of 1-oxa-2-magnesia-cyclohexane was evaluated by means of the obtained amount of n-butanol (as determined by gas-chromatography (GC)). Amount of n-butanol found (% of theory) after reaction time (hours; in brackets): 11.4 (51), 19.6 (99) and 25.4% (243).

In two parallel experiments, suspensions of 2.43 g (95 mmol) of the active magnesium in 75 ml THF were heated to reflux for 8 days, the excess of metal was removed by filtration, and to the filtrate there were added dropwise with stirring 50 mmol trimethylsilyl chloride or benzoylchloride, respectively, at $-78°$ C.

In the case of the silylation, the reaction mixture was then heated to reflux for 16 hours and thereafter the THF was evaporated under vacuum (14 mbar); the residue was extracted with pentane, the extract was concentrated under vacuum (14 mbar), and the remaining liquid was distilled at 83° C. to 85° C./14 mbar. There were obtained 3.92 g of 4-trimethylsilyl-butoxy-trimethylsilane (Speier, J. Am. Chem. Soc. 74, 1003 (1952)) (18% based on Mg), which was identified by its $^1$H-NMR spectrum (400 MHz, in CDCl$_3$): $\delta$ (ppm)= $-0.05$ (s, 9H), 0.08 (s, 9H), 0.47 (m, 2H), 1.32 (m, 2H), 1.52 (m, 2H) u. 3.55 (t, 2H).

In the case of the benzoylation, the reaction mixture was heated to reflux for 30 minutes; to the residue obtained after evaporation under 14 mbar at room temperature there was added ice water, and the mixture was extracted with ether. The ether extract was evaporated under vacuum at room temperature, and the remaining oil was distilled at 80° to 85° C./$10^{-5}$ bar. There were obtained 3.95 g of 4-benzoylbutylbenzoate (Tsuzumi et al. Jap. Pat. 77, 102, 204; Chem. Abstr. 88, 50515 (1978)) (14% based on Mg.), which was identified by its IR and $^1$H-NMR spectra: IR spectrum (film): 1733 and 1695 cm$^{-1}$. ($\nu$ C=O); $^1$H-NMR-Spektrum (80 MHz, in CDCl$_3$): $\delta$ (ppm)=1.88 (m, 4H), 3.02 (m, 2H), 4.33 (m, 2H), 7.2–7.7 (m, 6H) u. 7.75–8.2 (m, 4H).

EXAMPLE 3

2.43 g (0.10 mol) of the commercially available magnesium powder having a maximum particle diameter of 0.3 mm (50 mesh) were suspended in 0.6 l of absolute THF, and 32.2 g (0.18 mol) of anthracene and 0.06 ml of ethyl bromide were added to the suspension. After 1 hour of stirring at room temperature the orange precipitate of magnesium anthracene began to deposit. Stirring of the suspension was continued for another 48 hours; after filtration the filtercake was washed three times with 50 ml of THF each and dried under high vacuum. There were obtained 36.2 g of magnesium anthracene.3 THF (86.5%) as an orange microcrystalline powder.

A sample of 10.20 g (24 mmol) of magnesium anthracene.3 THF was first heated under high vacuum at 100° C. for 1 hour, in the course of which mainly THF was split off and condensed in a receiver cooled with liquid nitrogen. Then the temperature was increased to 150° C. during 4 hours, in the course of which the removal and sublimation of the anthracene occurred. Upon completion of the thermolysis, there were found 4.40 g (83%) of THF (GC analysis) in the receiver cooled with liquid nitrogen and recovered as sublimate 3.57 g (82%) of anthracene which was identified by its m.p. of 216° C. and by GC analysis. As the residue of the thermolysis there remained 0.52 g (88%) of a highly reactive black pyrophoric magnesium powder having the following composition (according to elementary analysis): Mg 93.6, C 5.3 and H 0.9%.

The specific surface aea of the magnesium powder (determined according to the BET method, N$_2$ as the adsorption gas) was 62.3 m$^2$/g.

0,42 g of the thus obtained active magnesium in a H$_2$ atmosphere under normal pressure at a temperature of 240° C. absorbed 318 ml of H$_2$ in the course of 2 hours and 358 ml of H$_2$ after a total of 19 hours (measured under 1 bar at 20° C.) to form magnesium hydride (MgH$_2$). The hydrogen uptake, based on the magnesium content of the sample, was 92%.

EXAMPLE 4

The experiment was carried out as in Example 2, however using the active magnesium obtained by the thermolysis of magnesium anthracene.3 THF (Example 3). The reaction of the active magnesium with THF to form 1-oxa-2-magnesia-cyclohexane proceeded at a similar rate as in Example 2.

EXAMPLE 5

2.30 g of isobutyl chloride (24.8 mmol) in 30 ml of toluene were dropwise added with stirring to a suspension of 0.65 g (27 mmol) of the active magnesium prepared according to Example 3 in 100 ml of toluene at room temperature within 45 minutes, and then the reaction mixture was heated at 70° C. with stirring for 2 hours. The suspension was filtered, and the filtercake was washed with pentane and dried under vacuum (0.2 mbar), whereafter 1.69 g of a solid were obtained which had the following composition (according to elementary analysis): C 32.2, H 5.4, Mg 26.4 and Cl 35.9%. 0.3883 g of this solid upon protolysis with 2-ethyl-1-hexanol and subsequently with 5N H$_2$SO$_4$ yielded 50.4 ml of a gas (0° C./1 bar) having the composition (analysis by mass spectrometry (MS)): isobutane 69.6 and H$_2$ 30.4%. From the isobutane content of the gas, a yield of isobutylmagnesiumchlorid, based on reacted (see below) isobutyl chloride of 32.7% is calculated. In the toluene solution there were analyzed (by GC or combined GC and MS analysis, respectively) 0.44 g (4.8 mol) of isobutyl chloride, 0.05 g (0.4 mmol) of C$_8$H$_{18}$- (2 isomers) and a total of 0.21 g (1.4 mmol) of C$_{11}$H$_{16}$-hydrocarbons (6 isomers, products of the Friedel-Crafts reaction).

In a control experiment, commercially available magnesium powder having a maximum particle diameter of 0.3 mm (50 mesh) did not display any reaction with isobutyl chloride under the same conditions (toluene; 70° C.; 2 hours).

EXAMPLE 6

Using 0.71 g (29.2 mmol) of active magnesium (Example 3) and 3.18 g (34.3 mmol) of isobutyl chloride in 130 ml of heptane, however otherwise in analogy of Example 5, the experiment was carried out and the mixture worked up. After filtration 1.71 g of a solid having the composition C 35.2, H 5.8, Mg 23.8 and Cl 35.0% was obtained. Hydrolysis of 0.3908 g of said solid yielded 30.0 ml of isobutane and 14.0 ml of H$_2$ (20° C./1 bar). The yield of isobutylmagnesium chloride, based on reacted (see below) isobutyl chloride was 31.6%. In the heptane solution there were found 1.50 g (16.2 mmol) of isobutyl chloride, 0.06 g (0.5 mmol) of $C_8H_{18}$-hydrocarbons (2 isomers) and 0.7 mmol of diisobutylmagnesium (8.3%).

EXAMPLE 7

A distillation apparatus equipped with a dropping funnel was charged with 10.4 g (25 mmol) of the magnesium anthracene.3 THF prepared as described in Example 3 in 300 ml of toluene; after stirring for 0.5 hours at room temperature the originally orange suspension changed its color to green yellow. The suspension was slowly heated to the boiling point of the mixture, while, beginning at about 70° C., the precipitation of a metallic-gray magnesium powder was observed. During 2 hours 538 ml of toluene distilled off while, to the same extent as the solvent distilled, fresh solvent was added dropwise. The precipitated magnesium powder was filtered off, washed with toluene and pentane and dried under vacuum (0.2 mbar). There were obtained 0.85 g (71% of theory) of an active magnesium powder which still contained anthracene. By GC analysis there were determined 5.23 g of THF (97.4% of theory) in the toluene removed by distillation, and 4.25 g of anthracene (96% of theory) in the filtrate.

EXAMPLE 8

A distillation apparatus equipped with a gas-introducing tube was charged with 14.7 g (66 mmol) of magnesium butadiene.2 THF (prepared according to Fujita et al. J. Organometal. Chem. 113, 201 (1976)) in 300 ml of toluene. In the course of warming up the suspension to the boiling temperature while passing argon therethrough, the precipitation of the metallic-gray magnesium powder was observed between 50° C. and 80° C. During 90 minutes with the argon stream 173 ml of toluene mixed THF were distilled; the gaseous products formed during the distillation (butadiene) were collected in a cooled trap (−78° C.) connected to the apparatus. The precipitated magnesium powder was separated by filtration, washed with toluene and pentane and dried under vacuum (0.2 mbar). There were obtained 1.48 g (92% of theory) of an active magnesium powder comprising 100% of Mg. 6.2 g of THF and 0.2 g of butadiene were found in the distilled toluene, and 1.0 g of THF and 1.4 g of butadiene were found in the condensate collected in the trap.

EXAMPLE 9

A solution of 2.2 g (20 mmol) of ethyl bromide in 10 ml of toluene was dropwise added to a suspension of 8.4 g (20 mmol) magnesium anthracene.3 THF in 50 ml of toluene at 0° C. with stirring in the course of 30 minutes. The suspension was allowed to warm up to room temperature, and then the precipitated anthracene was separated by filtration. 20.0 ml (of a total of 60.0 ml) of the solution, upon evaporation of the toluene under vacuum (0.2 mbar) and hydrolysis of the residue with water, yielded 136 ml (measured under 1 bar at 20° C.) of ethane (according to MS analysis), which correspond to a yield of 85% of ethylmagnesium bromide.

EXAMPLE 10

Using 10.5 g (25 mmol) of magnesium anthracene.3 THF, 1.9 g (25 mmol) of allyl chloride and 60 ml of THF the experiment was carried out in analogy of Example 9. The yield of allylmagnesium chloride, determined by means of the amount of propene formed upon hydrolysis, was 91%.

EXAMPLE 11

Using 4.1 g (9.8 mmol) of magnesium anthracene.3 THF, 0.75 g (9.8 mmol) of allyl chloride and 60 ml of ether the experiment was carried out in analogy of Example 9. The yield of allylmagnesium chloride, determined by means of the amount of propene formed upon hydrolysis, was 98%.

EXAMPLE 12

Using 8.4 g (20 mmol) of magnesium anthracene.3 THF, 1.5 g (20 mmol) of allyl chloride and 60 ml of toluene the experiment was carried out in analogy of Example 9. The yield of allylmagnesium chloride, determined by means of the amount of propene formed upon hydrolysis, was 81%.

EXAMPLE 13

A solution of 1.76 g (23 mmol) of allyl chloride in 40 ml of THF was dropwise added to a suspension of 9.6 g (23 mmol) magnesium anthracene. 3 THF in 100 ml of THF at −70° C. with stirring in the course of 1 hour, during which period the reaction mixture changed its color into deep blue. The deep blue suspension was subsequently stirred at −70° C. for 8 hours. Upon protolysis of the reaction mixture by addition of 5 ml of methanol at −70° C., there were recovered 370 ml (measured under 1 bar at 20° C.) of propene (according to MS analysis), which correspond to a yield of 67% of allylmagnesium chloride at a reaction temperature of −70° C.

What is claimed is:

1. In the formation of a compound including a —C—Mg—X moiety wherein X denotes a heteroatom selected from the group consisting of halogen, oxygen, sulfur, nitrogen, phosphorus, by reacting magnesium with a compound containing a poorly reacting —C—X moiety, the improvement which comprises using magnesium produced by thermally decomposing a magnesium-containing compound selected from the group consisting of
   (i) a magnesium anthracene and/or its derivatives prepared from magnesium and anthracene and/or its alkyl or phenyl derivatives,
   (ii) a magnesium butadiene and/or its alkyl or phenyl derivatives prepared from magnesium and a conjugated diene having the general formula $R^1$—CH=$CR^2$—CH=CH—$R^3$, wherein $R^1$, $R^2$ and $R^3$ are the same or different and represent H, a linear or branched alkyl group having from 1 to 6 carbon atoms or a phenyl residue, and
   (iii) a magnesium hydride-prepared from magnesium and hydrogen either in the presence of homogenous catalysts comprising a halide of a metal of the Subgroups IV to VII of the Periodic System and an organomagnesium compound or a magnesium hydride and in the presence of a polycyclic aromatic or a tertiary amine, after hydrogenating magnesium with magnesium anthracene or magnesium diene, said thermal decomposition taking place at a pressure from $10^{-6}$ to 1 bar and in the absence or presence of an organic aprotic solvent, either the decomposition being carried out in the presence of a co-reactant being added only after completion of the precipitation of the highly reactive magnesium, or in the absence of such co-reactant, the magnesium obtained by said decomposition being isolated as a highly reactive powder.

2. The process according to claim 1, wherein the decomposition of magnesium hydride is carried out in the absence of a solvent under a pressure of from 0.2 to 10 mbar at a temperature of from 250° C. to 300° C.

3. The process according to claim 1, wherein the decomposition of adducts of magnesium to conjugated dienes of the general formula $R^1—CH=CR^2—CH=CH—R^3$ is carried out in diethylether or dibutylether under a pressure of 1 bar and at a temperature of from $-100°$ C. to $+\pm150°$ C.

4. The process according to claim 1, wherein the decomposition of magnesium anthracene 3 THF or an alkyl or phenyl derivative thereof is carried out in the abesence of a solvent under a pressure of from $10^{-6}$ to $10^3$ bar at a temperature of from $+70°$ C. to $+170°$ C.

5. The process according to claim 1, wherein the decomposition of magnesium anthracene 3 THF or an alkyl or phenyl derivative thereof is carried out in an aliphatic, cycloaliphatic or aromatic hydrocarbon or in an open-chain aliphatic ether under a pressure of 1 bar and at a temperature of from $-100°$ C. to $+100°$ C.

6. The process according to claim 1, wherein said ether is selected from the group consisting of diethylether and dibutylether.

7. The process according to claim 1, wherein ethyl bromide, 1,2-dichloroethane, 1,2-dibromoethane and magnesium halides are used as promoters or catalysts, respectively, for the decomposition of said thermolabile magnesium compounds.

8. The process according to claim 1, wherein the decomposition of magnesium hydride is carried out in the absence of a solvent under a pressure of 1 bar at a temperature of from 250° C. to 350° C.

9. The process according to claim 1, wherein the decomposition of adducts of magnesium to conjugated dienes of the general formula $R^1—CH=CR^2—CH=CH—R^3$, wherein $R^1$, $R^2$ and $R^3$ are as defined above, is carried out in an aliphatic, cycloaliphatic or aromatic hydrocarbon or in an open-chain aliphatic ether under a pressure of 1 bar and at a temperature of from $-100°$ C. to $+150°$ C.

* * * * *